United States Patent
Bomberger et al.

(10) Patent No.: US 7,087,245 B2
(45) Date of Patent: *Aug. 8, 2006

(54) ICAM-1 FORMULATION HAVING CONTROLLED-SIZE MICROPARTICLES

(76) Inventors: David C. Bomberger, 2021 Arbor Ave., Belmont, CA (US) 94002; Paul G. Catz, 3332 Emerson St., Palo Alto, CA (US) 94306; Mark I. Smedley, 665 Catamaran, #2, Foster City, CA (US) 94404; Paul C. Stearns, 506 Oak Ave., Redwood City, CA (US) 94061

(*) Notice: Subject to any disclaimer, the term of this patent is extended or adjusted under 35 U.S.C. 154(b) by 0 days.

This patent is subject to a terminal disclaimer.

(21) Appl. No.: 10/128,147

(22) Filed: Apr. 22, 2002

(65) Prior Publication Data

US 2003/0091649 A1 May 15, 2003

Related U.S. Application Data

(60) Continuation of application No. 09/583,089, filed on Mar. 8, 1999, now Pat. No. 6,375,985, which is a division of application No. 08/480,624, filed on Jun. 7, 1995, now Pat. No. 5,879,712.

(51) Int. Cl.
*A61K 9/14* (2006.01)
*A61K 9/66* (2006.01)
*A61K 9/00* (2006.01)

(52) U.S. Cl. ............... 424/489; 424/455; 424/45; 424/43

(58) Field of Classification Search ........... 424/489, 424/455, 425, 45, 43; 514/772, 779, 789

See application file for complete search history.

(56) References Cited

U.S. PATENT DOCUMENTS

| | | | |
|---|---|---|---|
| 4,226,848 A | 10/1980 | Nagai et al. | 424/19 |
| 4,250,163 A | 2/1981 | Nagai et al. | 424/14 |
| 4,294,829 A | 10/1981 | Suzuki et al. | 424/241 |
| 4,364,515 A | 12/1982 | Prussin | 239/8 |
| 4,389,330 A | 6/1983 | Tice et al. | 427/213.36 |
| 4,814,161 A | 3/1989 | Jinks et al. | 424/45 |
| 4,835,142 A | 5/1989 | Suzuki et al. | 514/53 |
| 4,842,866 A | 6/1989 | Horder et al. | 424/468 |
| 5,059,587 A | 10/1991 | Yamamoto et al. | 514/12 |
| 5,079,005 A | 1/1992 | Gupta | 424/408 |
| 5,204,108 A | 4/1993 | Illum | 424/434 |
| 5,271,961 A | 12/1993 | Mathiowitz et al. | 427/213.31 |
| 5,292,499 A | 3/1994 | Evans et al. | 424/45 |
| 5,407,609 A | 4/1995 | Tice et al. | 264/4.6 |
| 5,476,663 A | 12/1995 | Okada et al. | 424/423 |
| 5,840,254 A | 11/1998 | Carver, Jr. et al. | 422/68.1 |
| 5,879,712 A * | 3/1999 | Bomberger et al. | 424/489 |
| 6,375,985 B1 * | 4/2002 | Bomberger et al. | 424/489 |

FOREIGN PATENT DOCUMENTS

| | | |
|---|---|---|
| EP | 0 362 531 A1 | 11/1990 |
| EP | 0 468 257 A1 | 1/1992 |
| WO | WO 91/06282 A1 | 5/1991 |
| WO | WO 96/03142 A1 | 2/1996 |

OTHER PUBLICATIONS

E. Björk et al., "Effect Of Degradable Starch Microspheres On The Human Mucociliary Clearance", *Proceed. Intern. Symp. Contol. Rel. Bioact. Mater.*, vol. 19, pp. 417–418, (no month).

J. D. Smart et al., "In Vitro Techniques for Measuring Mucoadhesion", J. Pharm. Pharmacol. (Supplement)., vol. 34, p. 70P, 1982 (no month).

H. Ch'hg et al., "Bioadhesive Polymers as Platforms for Oral Controlled Drug Delivery II: Synthesis and Evaluation of some Swelling, Water–Insoluble Bioadhesive Polymers", *Journal of Pharmaceutical Sciences*, vol. 74, No. 4, pp. 399–405, Apr. 1985.

A. Yapel, Jr., "Albumin Microspheres: Heat and Chemical Stabilization", *Methods in Enzymology*, vol. 112, pp. 3–18, 1985 (no month).

J. G. Hardy et al., "Intranasal drug delivery by spray and drops", *J. Pharm. Pharmacol.*, vol. 37, pp. 294–297, 1985 (no month).

M. Longer et al., "Fundamental aspects of bioadhesion", *Pharmacy International*, pp. 114–117, May 1986.

E. R. Morris, "Molecular Interactions in Polysaccharide Gelation", *British Polymer Journal*, vol. 18, No. 1, pp. 14–21, 1986 (no month).

A. S. Harris, "Biopharmaceutical Aspects on the Intranasal Administration of Peptides", Chapter in *Delivery Systems for Peptide Drugs*, S. Davis et al., editors, Plenum Press, pp. 191–204, Jan. 1987.

(Continued)

*Primary Examiner*—Thurman K. Page
*Assistant Examiner*—Blessing Fubara
(74) *Attorney, Agent, or Firm*—The Luther Law Firm; Barbara J. Luther

(57) ABSTRACT

Method and system of producing microparticles loaded with biologically active drugs, including proteins such as ICAM-1, for controlled release of the drugs in a nasal passageway. The method includes introducing a drug/polymer feed solution and an emulsifier into a first mixing chamber to create an emulsion, then mixing a cross-linking agent together with the emulsion under controlled conditions to create microparticles loaded with the drug. The system includes a first mixing chamber, in which the emulsion is created, having a first port for introducing the drug/polymer solution, and a second port angled substantially perpendicular to the first port for introducing the emulsifier. A second mixing chamber adjacent to the first mixing chamber receives the emulsion and either contains a cross-linking agent or receives a stream of a cross-linking agent to solidify the microparticles. The formed microparticles are filtered and deaggregated to form individual microparticles that then may be formulated for nasal passageway delivery.

3 Claims, 4 Drawing Sheets

OTHER PUBLICATIONS

L. Illum, "Microspheres As A Potential Controlled Release Nasal Drug Delivery System", Chapter in *Delivery Systems for Peptide Drugs*, S. Davis et al., editors, Plenum Press, pp. 205–210, Jan. 1987.

L. Illum et al., "Bioadhesvie microspheres as a potential nasal drug delivery system", *International Journal of Pharmaceutics*, vol. 39, No. 3, pp. 189–199, Oct. 1987.

A. K. Pennington, "The influence of solution viscosity on nasal spray deposition and clearance", *International Journal of Pharmaceutics*, vol. 43, pp. 221–224, 1988 (no month).

C. Robert et al., "Experimental Method for Bioadhesive Testing of Various Polymers", *Acta Pharm. Technol.*, vol. 34, No. 2, pp. 95–98, 1988 (no month).

E. Björk et al., "Degradable starch microspheres as a nasal delivery system for insulin", *International Journal of Pharmaceutics*, vol. 47, pp. 233–238, 1988 (no month).

L. Illum et al., "Nasal administration of gentamicin using a novel microsphere delivery system", *International Journal of Pharmaceutics*, vol. 46, pp. 261–265, 1988 (no month).

A. Martinsen et al., "Alginate as Immobilization Material: 1. Correlation between Chemical and Physical Properties of Alginate Gel Beads", *Biotechnology and Bioengineering*, vol. 33, pp. 79–89, 1989 (no month).

K. K. Kwok et al., "Sterile Microencapsulation of BCG In Alginate–Poly–L–Lysine By An Air Spraying Technique", *Proceed. Intern. Symp. Control. Rel. Bioact. Mater.*, vol. 16, pp. 342–343, 1989 (no month).

L. Illum et al., "Enhanced nasal absorption of insulin in rats using lysophosphatidylcholine", *International Journal of Pharmaceutics*, vol. 57, pp. 49–54, 1989 (no month).

H. J. Lewis et al., "Nasal Peptide Delivery By Mucoadhesive Polymers", *Proceed. Intern. Symp. Control. Rel. Bioact. Mater.*, vol. 17, pp. 289–290, 1990 (no month).

"Kelco Products In Controlled Release Applications", Kelco, a Division of Merk & Co., Inc., RC–171, pp. 1–7, 1990 (no month).

T. Nagai et al., Chaper 9 "Bioadhesive Dosage Forms For Nasal Administration", V. Lenaerts et al Editors., *Bioadhesive Drug Delviery Systems*, CRC Press, Inc., pp. 169–178, 1990 (no month).

T. Todisco et al., "Fate of Human Albumin Microsphere and Spherocyte Radioaerosols in the Human Tracheobronchial Tree", *Lung*, Suppl., pp. 665–671, 1990 (no month).

L. Illum et al., "The nasal delivery of peptide and proteins", *TIBTECH*, vol. 9, pp. 284–289, Aug. 1991.

A. Al–Shamkhani, "Evaluation Of The Biological Properties Of Alginates And Gellan And Xanthan Gums", *Proceed. Intern. Symp. Control. Rel. Bioact. Mater.*, vol. 18, pp. 213–214, 1991 (no month).

M. A. Wheatley et al., "Coated Alginate Microspheres: Factors Influencing the Controlled Delivery of Macromolecules", *Journal of Applied Polymer Science*, vol. 43, pp. 2123–2135, 1991 (no month).

C. Champagne et al., "*Lactococcus lactis* Release from Calcium Alginate Beads", *Applied and Environmental Microbiology*, vol. 58, No. 5, pp. 1429–1434, May 1992.

L. Rydén et al., "Effect of polymers and microspheres on the nasal absorption of insulin rats", *International Journal of Pharmaceutics*, vol. 83, No. 1–3, pp. 1–10, Jun. 1992.

G. Wolters, "A Versatile Alginate Droplet Generator Applicable for Microencapsulation of Pancreatic Islets", *Jr. of Applied Biomaterials*, vol. 3, pp. 281–286, 1992 (no month).

K. V. Roskos, "Method For Screening New Bioadhesive Functionalities", *Proceed. Intern. Symp. Control. Rel. Bioact. Mater.*, vol. 19, pp. 86–87, 1992 (no month).

L.S.C. Wan et al., "Drug encapsulation in alginate microspheres by emulsification", *Microencapsulation*, vol. 9, No. 3, pp. 309–316, 1992 (no month).

P. Vidgren et al., "In Vitro Evaluation Of Spray–Dried Mucoadhesive Microsphers For Nasal Administration", *Drug Development And Industrial Pharmacy*, vol. 18, No. 5 pp. 581–597, 1992 (no month).

G. Lee et al., "Stability of Antibody Productivity Is Improved When Hybridoma Cells Are Entrapped in Calcium Alginate Beads", *Biotechnol Bioeng.*, vol. 42, No. 9, pp. 1131–1135, Nov. 1993.

H. Kublik et al., "Rheological Properties of Polymer Solutions as Carriers for Nasal Drug Delivery Systems", *Eur. J. Pharm. Biopharm.*, vol. 39, No. 5, pp. 192–196, 1993 (no month).

S. Shiraishi et al., "Controlled–Release Preparation of Indomethacin Using Calcium Alginate Gel", *Biol. Pharm. Bull.*, vol. 16, No. 11, pp. 1164–1168, 1993 (no month).

A. Polk et al., "Controlled Release of Albumin from Chitosan–Alginate Microcapsules", *Journal of Pharmaceutical Sciences*, vol. 83, No. 2, pp. 178–185, Feb. 1994.

S. Sugaware et al., "The Controlled Release of Prednisolone Using Alginate Gel", *Pharmaceutical Research*, vol. 11, No. 2, pp. 272–277, 1994 (no month).

* cited by examiner

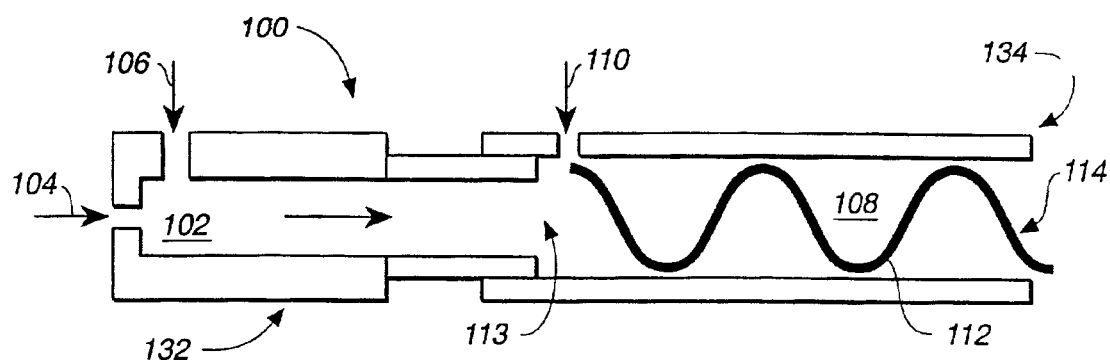
FIG._1
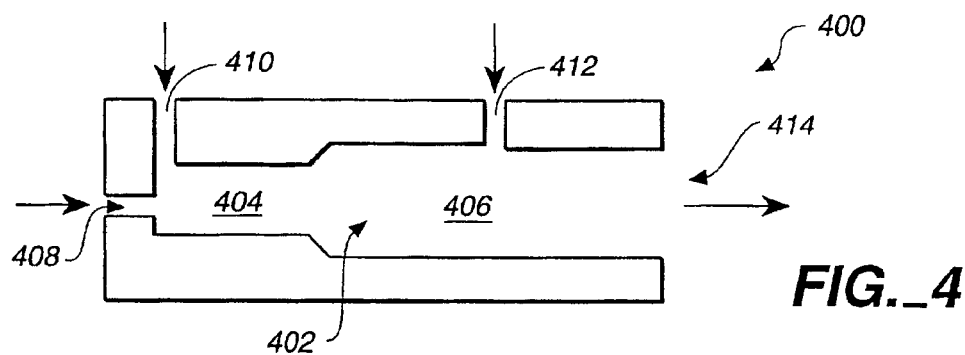
FIG._4
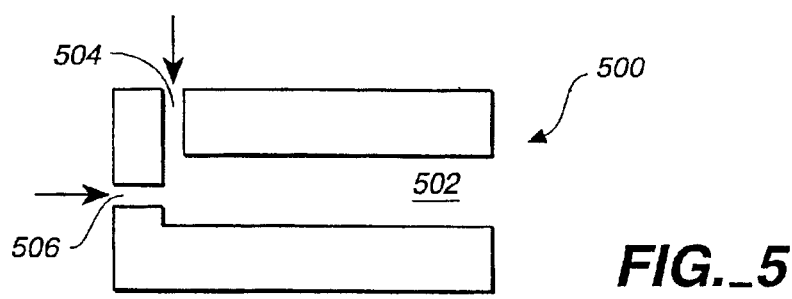
FIG._5
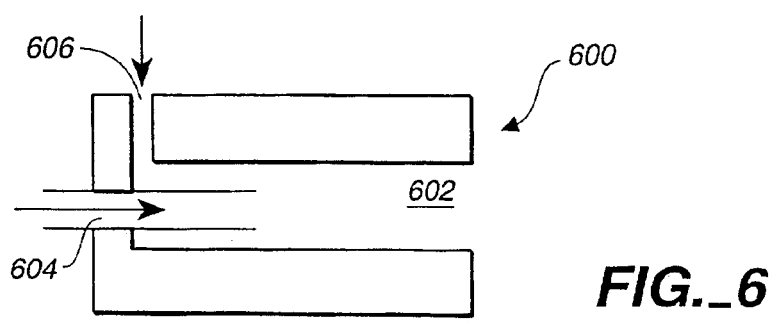
FIG._6

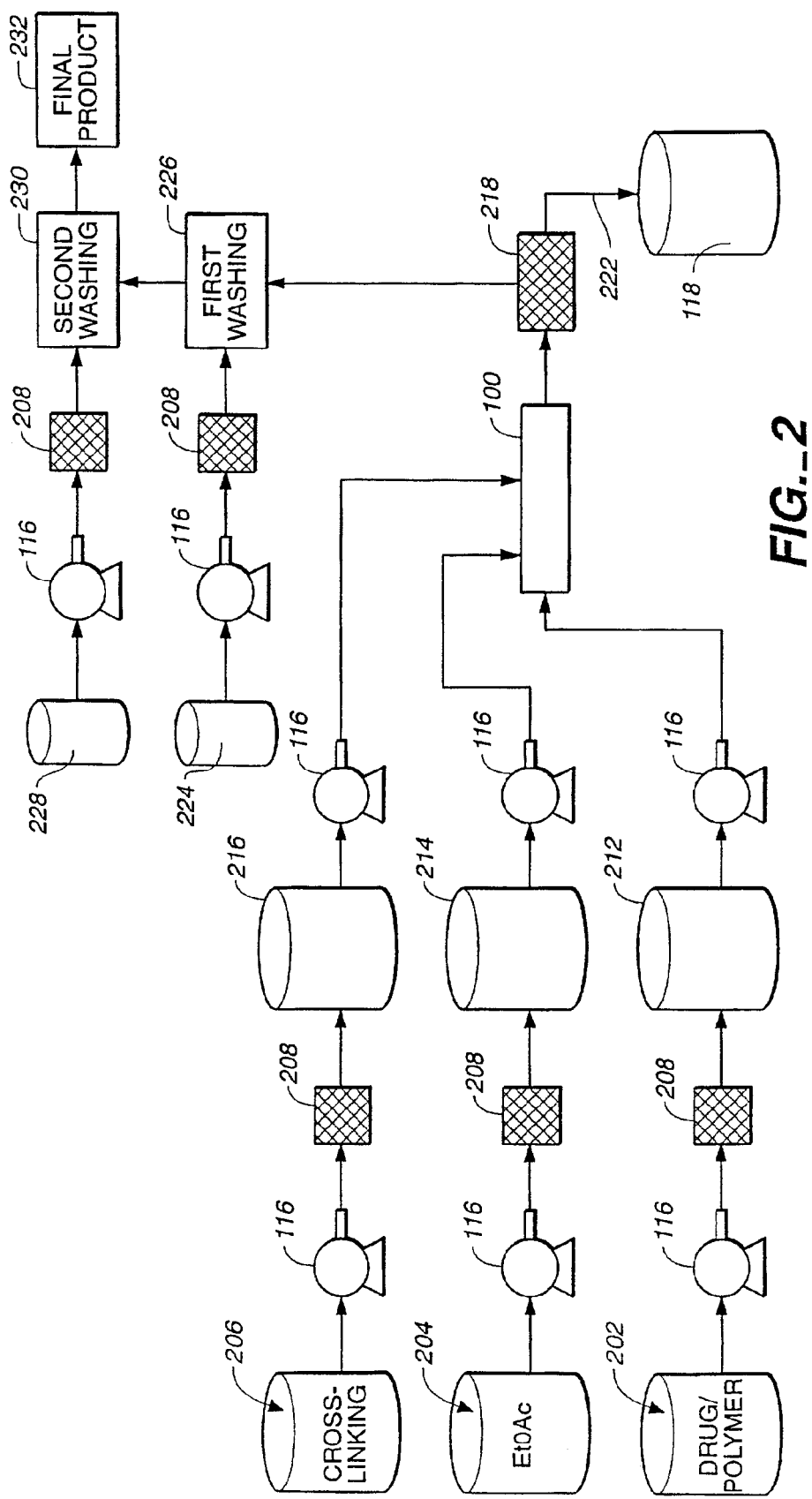
FIG._2

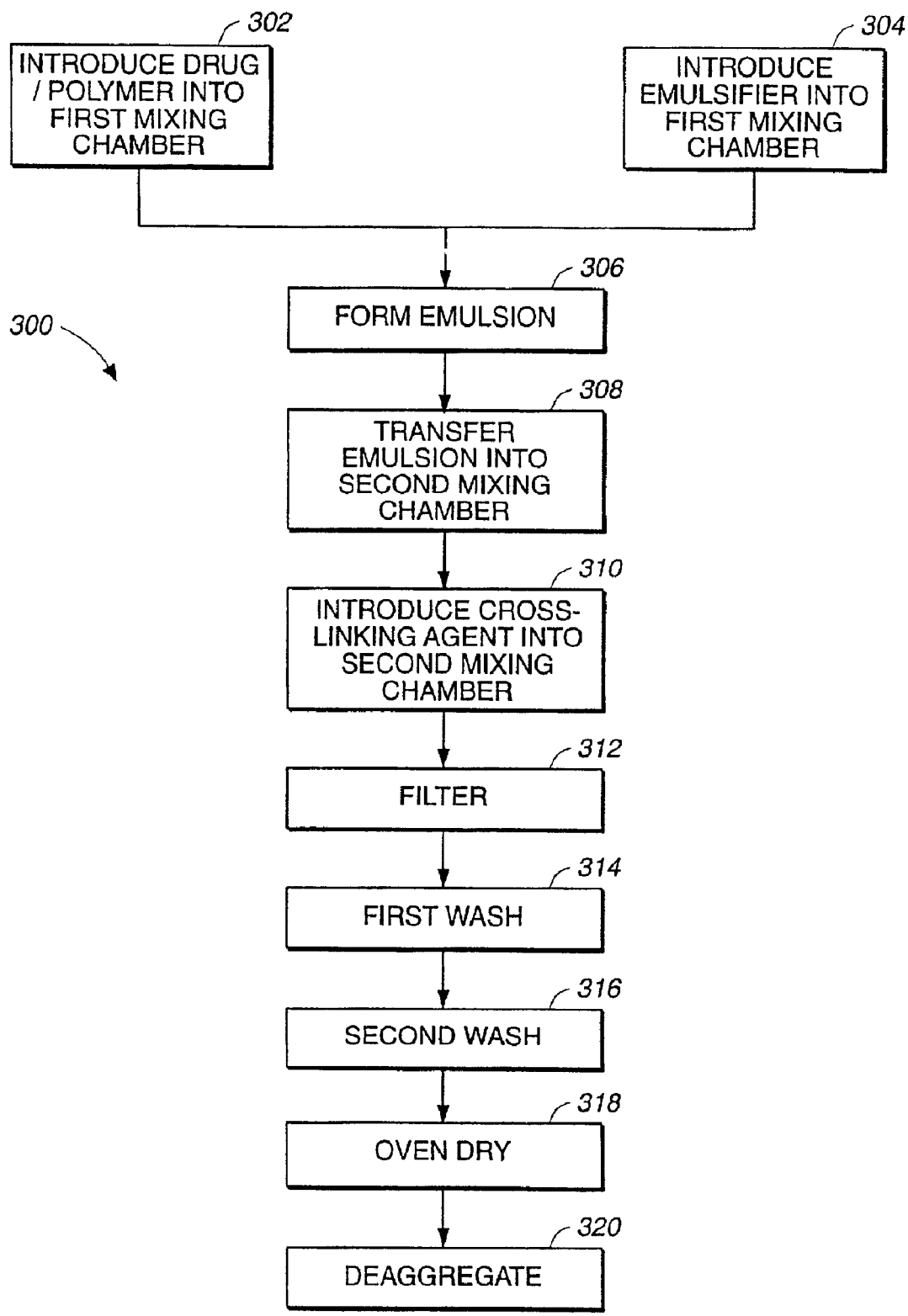
FIG._3

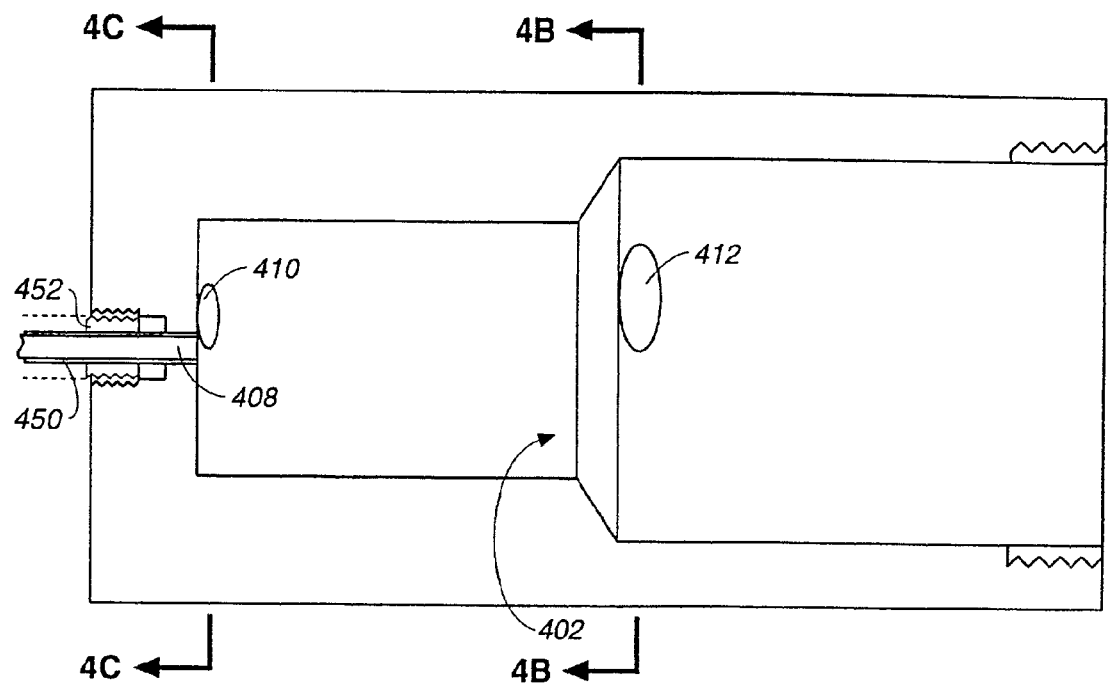
FIG._4A
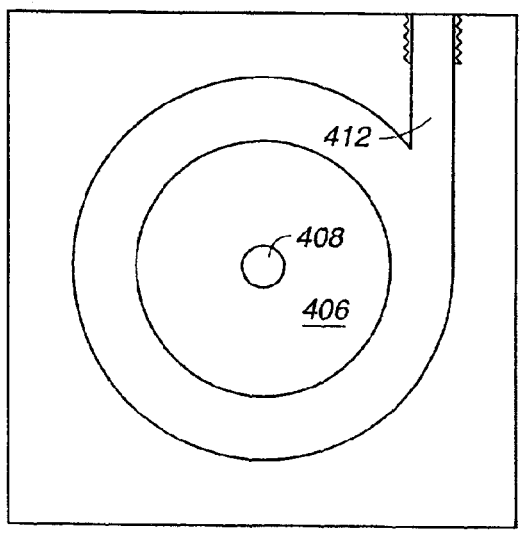 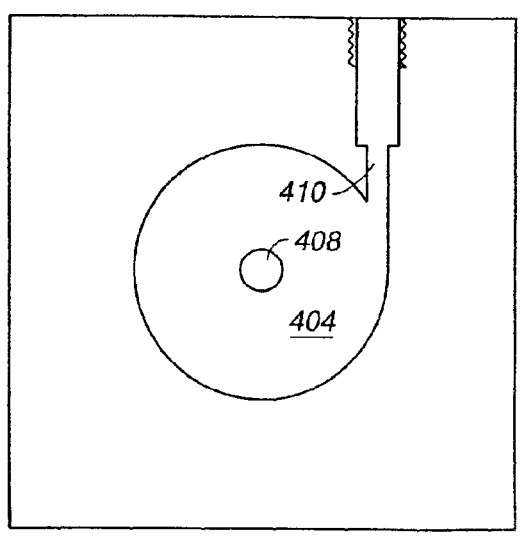
FIG._4B     FIG._4C

ICAM-1 FORMULATION HAVING CONTROLLED-SIZE MICROPARTICLES

CROSS-REFERENCE TO RELATED APPLICATIONS

This application is a continuation of application Ser. No. 09/583,089, filed Mar. 8, 1999, now U.S. Pat. No. 6,375,985, issued Apr. 23, 2002, which is a divisional application of application Ser. No. 08/480,624, filed Jun. 7, 1995, now U.S. Pat. No. 5,879,712, issued Mar. 9, 1999.

TECHNICAL FIELD

The present invention relates generally to the field of producing drug-loaded microparticles, and relates specifically to the field of producing microparticles that yield a sustained, controlled release of the drug over a period of time. More specifically, the present invention relates to a system and method of loading microparticles with intercellular adhesion molecule ICAM-1, one or more functional domains of ICAM-1, one or more biologically active ICAM-1 fragments, analogs of such biologically active ICAM-1 fragments, and combinations and functional derivatives thereof, and which microparticles are deposited in the nasal cavity and yield a sustained, controlled release of ICAM-1 over several hours.

BACKGROUND OF THE INVENTION

In recent years, the nasal passageway has been gaining attention as an alternate route of administration for systemically active drugs, such as peptides and proteins. Some proteins, such as intracellular adhesion molecule ICAM-1, are best delivered via the nasal passageway.

The desired size range of microparticles that maybe used to deliver drugs via the nasal passageway is fairly narrow, i.e., diameters of between about 20 µm and 80 µm. If the microparticles are too small, i.e., less than about 10 µm, they can be carried with the airstream down into the tracheobronchial region. Thus, microparticles having diameters of less than about 10 µm could be used to deliver drugs via the tracheobronchial passageways. If the microparticles are too large, i.e., greater than about 100 µm, then the microparticles are relatively rapidly cleared from the nasal passageway.

Drug delivery to the nasal mucosa, for either topical or systemic action, is influenced by the duration of the contact with the drug-loaded particles. Nasal spray preparations administered using pumps or pressurized metered dose inhalers deposit mainly in the anterior part of the nasal cavity. That region is largely non-ciliated, and clearance is relatively slow. Generally, mucociliary function clears materials from the turbinates into the nasopharynx on average at a rate of about 6 mm/minute, with the flow rate increasing posteriorly. Nasal clearance depends on the particle size of the drug-loaded particles and the deposition site within the nasal passageway. Particles deposited in the sparsely ciliated or non-ciliated anterior region of the nasal cavity are cleared at a slower rate due to a slow drag from the contiguous mucus.

The majority of human rhinoviruses, the major causative agent of the common cold, utilize intercellular adhesion molecule 1 (ICAM-1) as a receptor on host cells. ICAM-1 is an integral membrane protein with a large N-terminal extracellular portion, a transmembrane anchor, and a short C-terminal cytoplasmic domain. The normal physiological function of ICAM-1 is to serve as a membrane-bound ligand of the leukocyte integrin lymphocyte function-associated antigen 1 (LFA-1) and mediate intercellular adhesion between leukocytes and a variety of cell types. (See, Greve et al., "Mechanisms of Receptor-Mediated Rhinovirus Neutralization Defined by Two Soluble Forms of ICAM-1", *J. Virol.* 65(11):6015–6023 (1991)). Since ICAM-1 binds human rhinovirus, a truncated form of ICAM-1, t-ICAM-453, has been proposed for clinical use as a nasally delivered prophylactic for rhinovirus infections. It would be desirable to minimize the need for repeated administration by providing increased ICAM-1 dwell-time in the nasal cavity.

The technology of microparticle production has extensive applications for drug delivery. A number of techniques have been utilized to make such microparticles, including solvent evaporation, and spray drying. One of the simplest presently available techniques is the preparation of calcium alginate microparticles by extruding or spraying sodium alginate solution as droplets into a calcium chloride solution.

The acceptability of microparticles for controlled release of drugs, including proteins, in the nasal passageway requires a product that is small in diameter, i.e., considerably less than one millimeter, that may be manufactured in a consistent size and drug distribution, and that has controlled degradation properties.

One method for manufacturing calcium alginate microparticles is to disperse the aqueous sodium alginate solution containing drug in an organic phase, then add calcium chloride to harden the emulsion formed droplets. In one such batch-process, a 3:2 ratio of two surfactants (sorbitan trioleate and polyoxyethylene sorbitan trioleate) and a minimum concentration of approximately 1% weight/weight (w/w) of surfactant is required to be added to the mixture to produce acceptable drug-loaded particles. (See, e.g., Wan et al., "Drug Encapsulation in Alginate Microspheres by Emulsification." *Microencapsulation* 9(3):309–316 (1992)). Other surfactant mixture ratios or concentrations may affect the microparticle size, shape, degree of clumping, drug loading and drug release characteristics. Thus, this method of preparing calcium alginate microparticles is sensitive to surfactant types and concentrations.

In batch process emulsion formation and hardening techniques, surfactants commonly are required to improve the microparticle size/shape and drug encapsulation efficiency. Problems likely to arise as a result of using such surfactants include: difficulty in washing the surfactants out of the formulation and measuring residual levels; possible adverse health effects caused by any residual surfactants; difficulty in washing the surfactants out of the formulation while not leaching out the drug; and potential effects on the bioadhesion, swelling behavior, and drug release profile of the microparticle.

Spray droplet formation techniques for manufacturing microparticles tend to produce large particles, i.e., over one millimeter (1 mm) in diameter. Although spray droplet formation techniques could be used to produce microparticles in the desired size range of between about 20 µm and 80 µm, this droplet formation technique is not desirable due to the difficulty in scaling the technique, process variability, and lack of suitability to clean pharmaceutical processing.

Numerous chemicals, polymers and controlled-release agents that may be used in manufacturing microspheres are known and commercially available. Examples of materials used to prepare microspheres for nasal delivery are: cellulosic polymers, specifically lower alkyl ethers of cellulose, starch, gelatin, collagen, dextran and dextran-derivatives, protein polymers, such as albumin, disodium cromoglycate, sephadex, or DEAE-sephadex. These may include mixtures or coatings with other materials such as polyacrylic acids, to improve the bioadhesive or controlled-release properties of the microspheres. (See, e.g., U.S. Pat. No. 5,204,108 to Illum.)

Other materials that may be used in manufacturing microparticles are known and include alginates, xanthan gum, and gellan gum, among others. All three substances are effective as enteric coatings. Alginates are known to produce uniform films, with application in industries as diverse as paper coatings, textile printing, and foods. The alginate film is particularly useful as an enteric coating because it normally is applied as the soluble sodium form, which then is converted to the insoluble alginic acid form by gastric fluids. Improvements have been made by combining sodium alginate with sodium calcium alginate in tablets containing high drug loading.

Alginates also have been used in fluid suspensions for many years because of their ability to form a gel upon contact with gastric fluids. Furthermore, calcium alginate gel beads are used to contain a variety of substances, such as flavors in the food industry, enzymes for bioreactors, live cells, and live organisms. Calcium alginate is particularly favored because of the mild conditions employed in its manufacture and the nontoxicity of the reagents.

Alginate is a collective term for a family of copolymers containing 1,4-linked β-D-mannuronic and α-L-guluronic acid residues in varying proportions and sequential arrangement. Alginate forms gels with divalent ions like calcium, and the gel-forming properties are strongly correlated with the proportion and lengths of the blocks of contiguous L-guluronic acid residues in the polymeric chains. The properties of alginates are described in Martinsen et al., "Alginate as Immobilization Material," *Biotechnol Bioeng.* 33:79–89 (1989).

Although there are several reports of using alginate beads to microencapsulate peptides and proteins, nearly all reports indicate bead sizes over 100 μm in diameter. In addition, nearly all reports prepare alginate gel beads by dropping sodium alginate solution into an aqueous calcium chloride solution to form the beads. While such a method does produce microencapsulated beads, the difficulty in controlling operating conditions to produce microparticles in the desired size range, difficulty in scaling, and the lack of suitability to clean pharmaceutical processing makes such methods impractical for commercial production of microparticles containing proteins such as ICAM-1.

The preparation of drug-loaded microspheres is described generally in U.S. Pat. No. 5,204,108 to Illum. In that patent, active agents are incorporated into microspheres made from gelatin, albumin, collagen, dextran and dextran-derivative. The final microspheres are cross-linked and finally processed for transmucosal delivery. However, there remains a need for microspheres that deliver a drug to the nasal passageway for controlled, long-term release of the drug in the passageway and that neither cross the mucosal barrier nor are cleared from the passageway.

Thus, there remains a need for a method and system for producing microparticles loaded with drugs, peptides or proteins that may be used for controlled, sustained release of the drug or protein. The preferred method and system should reliably produce microparticles for delivery of drug into the nasal passageway that have a predictable load, that are within a size range of between about 20 μm and about 80 μm, with about an 80% to about 100% recovery, and without significant loss in drug efficacy.

SUMMARY OF THE INVENTION

The present invention relates to a system and method of manufacturing alginate microparticles loaded with a drug, including a protein such as intercellular adhesion molecule ICAM-1, that can be delivered via the nasal passageway.

The system of the invention comprises a semi-continuous flow system that mixes a drug-loaded, alginate stream, most preferably a low viscosity sodium alginate (LVCR), with an emulsifier stream to form an emulsion in a mixing chamber. At a point downstream either in the same or an adjacent mixing chamber, a stream containing a cross-linking agent, such as a calcium salt, is added to the emulsion. In the cross-linking process, sodium in the sodium alginate is replaced by calcium, forming a non-water soluble calcium alginate microparticles loaded with the drug. After collection, the microparticles are filtered, washed, dried in a vacuum oven and, if necessary, deaggregated using gentle pressure to produce individual drug-loaded microparticles that may be delivered via the nasal passageway.

The system and method of the invention produces microparticles having diameters of between about 20 μm and about 80 μm, with diameters preferably between about 40 μm and about 50 μm, with an ICAM-1 loading of about 10% by weight. The system yield is up to about 100%.

BRIEF DESCRIPTION OF THE DRAWINGS

FIG. 1 shows a schematic representation of a longitudinal cross-section representative mixing block embodying the present invention.

FIG. 2 shows a schematic of a method and system embodying the present invention.

FIG. 3 is a flow chart of one embodiment of the method of the present invention.

FIG. 4 shows a schematic representation in longitudinal cross-section of a representative mixing block embodying the present invention.

FIG. 4A shows in longitudinal cross-section the mixing block of FIG. 4, with tubing and mylar fittings.

FIG. 4B is a cross-section taken along lines 4B—4B of FIG. 4A.

FIG. 4C is a cross-section taken along lines 4C—4C of FIG. 4A.

FIG. 5 shows in longitudinal cross-section a representative second mixing block with the second mixing chamber of a system embodying the present invention.

FIG. 6 shows in longitudinal cross-section a representative second mixing block with the second mixing chamber of a system embodying the present invention.

DESCRIPTION OF SPECIFIC EMBODIMENTS

The present invention relates to a novel system and method for producing microparticles loaded with a desired drug or protein, such as ICAM-1, which may be delivered via a nasal passageway for controlled release of the drug.

Most drug delivery systems using the nasal passageway, seek to increase the systemic transfer of the drug. The mechanism of the protein intercellular adhesion molecule ICAM-1 requires that the particle stay on the surface of the nasal passageway, neither absorbing into the host system nor being cleared by the efficient nasal clearance system. Thus, for ICAM-1, it is important to identify a system for producing ICAM-1 loaded microparticles that can be delivered to a nasal passageway, and that will remain within the passageway for an amount of time to permit the ICAM-1 molecule to bind to the target rhinovirus molecule before the ICAM-1 is absorbed or otherwise cleared.

The system described herein reliably produces microspheric particles having diameters in the range of between about 20 μm and about 80 μm, preferably with diameters in the range of between about 40 μm and about 50 μm, and with an approximate drug loading of 10% by weight and an ICAM-1 recovery rate greater than about 80%.

Referring to FIG. 4 of the drawings, a preferred embodiment of the system of the invention generally includes a mixing block having first and second axially connected, cylindrical mixing chambers disposed therein. The diameter of the second chamber is preferably somewhat larger than that of the first chamber. A first stream of drug/polymer solution is introduced axially into the first chamber through a first longitudinal, axial port located in the end wall of the first chamber distant from the second chamber. A second stream of emulsifier is introduced into the first chamber through a second port, positioned adjacent the same end of the first chamber as the first port for injecting the second stream substantially orthogonal to and off-set from the first stream. Preferably the second port is positioned for injecting the second stream tangentially to the cylindrical wall of the first chamber. The end of the second cylindrical chamber opposite the first chamber is open so that liquid can exit the second chamber smoothly, without eddy effects.

The flow rates of the first and second streams and the dimensions of the first and second chambers are such that both chambers fill with the injected liquids. Thus, the injected liquids flow from the first and second ports through the first and second chambers and out a third port formed by the open end of the second chamber. The emulsifier stream injected tangentially through the second port also has an axial velocity component from the liquid flow through the chambers, thereby resulting in a generally helical path. This results in a controlled turbulence within the first chamber sufficient to create an emulsion of droplets formed by the drug/polymer solution contacting the emulsifier upon entering the first chamber, but without significantly reducing the size of the initially formed droplets.

In the second chamber the droplets are cross-linked by a cross-linking agent that is introduced via a fourth port positioned such that a stream of cross-linking solution including the cross-linking agent is injected into the second chamber orthogonal to and off-set from the longitudinal axis of the second chamber. Preferably, the fourth port is positioned for injecting the cross linking stream tangentially to the cylindrical wall of the second chamber for creating a turbulent helical flow of the cross linking agent.

Several parameters potentially affect the success of such a system. For example, solvent properties, such as polarity and hydrophilicity, have a potential impact on miscibility, drug loading, and interaction with the aqueous emulsion. Flow rates into the mixing chambers of the system have a potential effect on the mixing characteristics and turbulence within the mixing block, which in turn affects microparticle size, size distribution of the microparticles, and the likelihood of clumping within the mixing chambers. Concentration of the cross-linking agent has a potential effect on the speed and thoroughness of the cross-linking process. Washing and filtering processes have a potential effect on drug leaching, small particle loss, and microparticle agglomeration.

As used herein, the following abbreviations and terms include, but are not necessarily limited to, the following definitions:

"ICAM-1" shall mean intercellular adhesion molecule ICAM-1, and is used to denote both full length (transmembrane) and truncated (non-transmembrane) forms of ICAM-1, specific biologically active fragments, and functional analogs combinations and derivatives thereof, and including specifically t-ICAM-453.

"LVCR" shall mean low viscosity sodium alginate.

"Microparticle" shall mean a small, substantially solid agglomeration of a target drug and a polymer than have diameters between about 20 μm and about 80 μm, and that are consistent in size and drug distribution and with controlled degradation properties.

"Reynolds number" is a dimensionless number which is significant in the design of a model of any system in which the effect of viscosity is important in controlling the velocities or the flow pattern of a fluid, as expressed by the formula:

$$\frac{DVL}{\mu}$$

wherein D equals the density of a fluid, V equals the velocity of the fluid, L equals the diameter of the port or chamber through which the fluid is moving, and μ equals the fluid viscosity.

"Alginate" shall mean a family of copolymers containing 1,4-linked β-D-mannuronic and α-L-guluronic acid residues in varying proportions and sequential arrangement.

"Drug" shall mean any substance intended for use in the diagnosis, cure, mitigation, treatment or prevention of disease, including any pharmacologically active proteins and peptides, and including small molecules, hormones, polypeptides, vaccines, and components thereof.

"Emulsion" shall mean the result of the combination of two immiscible liquids, such as ethyl acetate and LVCR, where one liquid is dispersed as small droplets in the other liquid.

The embodiment of the system of the invention illustrated in cross-section in FIG. 1, is a semi-continuous flow system including a mixing block (100) having axially connected cylindrical mixing chambers (102, 108) and ports (104, 106, 110) formed therein. As shown in FIG. 1, the mixing block (100) includes a first mixing block (132) with a first mixing chamber (102) therein, and a second mixing block (134) with a second mixing chamber (108) therein. The second mixing chamber (108) includes a plurality of passageways (110, 113) for passing the emulsion and a cross-linking solution therethrough. The two blocks (132, 134) may be separate blocks that are joined via either flexible tubing or a rigid passageway. Alternatively, and as discussed below in connection with FIG. 4, the two mixing chambers (102, 108) may be incorporated into a single mixing block.

In a preferred embodiment, the mixing blocks (132, 134) are formed of a non-metallic material, such as Teflon™ or Delrin™, both of which are generally commercially available. Alternatively, the inner surfaces of the mixing chambers (102, 108) may be coated with or formed from a non-stick material, such as Teflon™, Delrin™, or another non-wetting synthetic material, since sodium or calcium alginate may precipitate on metallic surfaces, which could lead to blockage of one or more of the ports (104, 106, 110, 113) if they had metal surfaces. For example, when a cross-linking solution containing calcium salt in acetone or ethanol comes in contact with a polymer in the presence of metal, surface effects from the metal cause agglomeration of the microparticles and clogging of the ports. Another alternative would be to use a Teflon™ tube insert in the chambers (102, 108, 110) and internal third port (113) to reduce the surface effects with metal.

In one embodiment, the second mixing chamber (108) includes an in-line static mixer (112) to increase turbulence in that chamber (108). The mixer (112) may be a helix with abrupt edges that provides a tortuous path for the in-flowing emulsion. Other devices may be used to increase the emulsion flow through and/or into the second chamber (108) and to increase the turbulence within that chamber (108). However, it may be possible to create sufficient turbulence without an additional mixer apparatus by adjusting the flow rates of the streams through the various ports (104, 106, 110, 113).

The mixing block (100) may be any size appropriate for commercial scale manufacturing. In the illustrated embodiment of FIG. 4, the solid block (400) is manufactured from Delrin™, and measures approximately 7.6 cm by 5.1 cm by 5.1 cm. In that embodiment, the diameter of the front chamber (404) is 0.32 cm (0.125 in.), and the diameter of the wider chamber (406) is 0.48 cm (0.19 in.). The total interior length of the chamber (402) is about 8.4 cm (3.5 inches). Other sizes may be used, as desired, with appropriate parameter adjustments. In that illustrated embodiment, the mixing block (400) has a single mixing chamber (402), with a first "panhandle" segment (404) and a larger segment (406). The arrows indicate the direction of stream flows into and out of the chamber (402). The total length of the mixing block (400) is about 5.1 cm, and the narrow segment of mixing chamber (404) is about 0.32 cm in diameter, widening to about 0.48 cm in diameter in the larger segment (406).

Basically, a first port (104) lies along the horizontal axis of the block (100). A drug/polymer solution, discussed in further detail below, is introduced at a predetermined flow rate through first port (104) and into the first mixing chamber (102). A second port (106) is positioned essentially orthogonal to the interior wall of the first chamber (102) and off-set from the line of the stream flowing from the first port (104). An emulsifier is introduced at a predetermined flow rate through this port (106) and into the first mixing chamber (102) to form an emulsion with the drug/polymer solution within the first mixing chamber (102). In the illustrated embodiment of FIG. 4, both ports (408, 410) have the same inner diameter of 0.034 cm.

It is possible to vary the inner diameter of one port over the other and adjust the relative flow rates of the two components and still achieve microparticles of a desired mean diameter. A small change in the inner diameter of one port can affect the turbulence, as expressed by the Reynolds number, and thus affect the size of the resulting microparticles.

The port (412) through which the cross-linking solution is introduced is offset from the line of the emulsion stream, and has a slightly larger diameter than the other two ports, i.e., about 0.16 cm.

As illustrated in FIG. 4A, which is enlarged and not drawn to scale, the ports each have a normal pipe thread (NPT) fitting (452), such as Swagelok® fittings, fitted with tubing (450) leading into the mixing chamber (402). In that illustrated example, tubing (450) is secured within an NPT fitting (452) at each of the ports (408, 410, 412). At ports (408, 410), the port diameter preferably is smaller than the inner diameter of the tubing so there is no flow disruption of the drug/polymer solution as it enters the chamber (402).

Turbulence created by the respective streams of solution flowing from the ports (408, 410) assist in assuring that most of the polymer comes into contact with the emulsifier. As the emulsion is formed, it moves into the larger segment of the mixing chamber (406), where it encounters a stream of cross-linking agent flowing from the tertiary port (412). The turbulence generated in that segment of the mixing chamber (406) is generated by the cross-linking solution stream and the flow of the emulsion from the panhandle segment of the mixing chamber (404). The resulting microparticles and solvent than are expressed through the exit power (414) of the larger segment of the chamber (406).

FIG. 4C, which is enlarged and not drawn to scale, shows the mixing chamber (404) in cross-section. In that illustrated embodiment, the first port (408) lies along the longitudinal axis and introduces the drug/polymer solution stream into the "panhandle" portion (404) of the chamber. The second port (410), through which an emulsifier is introduced, is aligned such that the outer wall of the second port (410) is orthogonal to the inner wall of the chamber (404), to introduce the emulsifier stream tangential to the stream of drug/polymer solution. As illustrated, the second port (410) is off-set from the alignment of the first port (408).

The off-set amount of the second port (410) from the first port (408) is sufficient to generate a turbulence within the chamber at (404) of drug/polymer droplets and emulsifier. Most preferably, the respective streams from ports (408) and (410) do not intersect. The forward motion of the stream from port (408), combined with the tangential motion of the stream from port (410) form a helical pathway through the narrower portion (404) of the chamber and into the larger portion (406) of the chamber, and ultimately out the exit port of block (414).

Similarly, and as shown in FIG. 4B, the third port (412) is positioned substantially orthogonal to the inner chamber (406) and off-set from the stream of emulsion entering the chamber (406).

The introduction of both the drug/polymer solution and the emulsifier along the same axis, i.e., coaxial introduction of the two solutions into the first mixing chamber does not produce microparticles of the desired size. The amount of turbulence established within the first mixing chamber (102) is affected by the direction of introduction of the emulsifier and the drug/polymer solution. The introduction of the emulsifier stream substantially tangential to the wall of the chamber (102) and off-set from the drug/polymer solution stream creates sufficient turbulence to produce microparticles of the desired size range.

FIG. 5 shows an alternate embodiment of a second mixing block (500) containing a second mixing chamber (502) for introducing a stream of cross-linking agent into emulsion moving from a first mixing chamber (not shown) into the second mixing chamber (502) through an inlet port (506). In the illustrated embodiment, a standard short tube design is used to introduce the emulsion from the first mixing chamber (not shown) into the second mixing chamber (502).

The diameter of the illustrated mixing chamber (502) is about 0.95 cm. The port (504) is positioned to introduce the cross-linking agent tangential to the cylindrical wall thereof, thereby producing a turbulent helical flow therein. Port (504) is not off-set from the port (506) through which the emulsion enters the chamber.

FIG. 6 illustrates an alternate embodiment of a second mixing block (600) containing a second mixing chamber (602) into which the cross-linking agent and the emulsion are introduced. In that embodiment, an annular mixing tee (604) is used to introduce the emulsion from the first mixing chamber (not shown) into the second mixing chamber (602).

The outer diameter of the annular tee (604) is about 0.64 cm, and the inner diameter of the mixing chamber (602) is about 0.95 cm. The diameter of the port (606) through which the cross-linking agent is introduced is about 0.95 cm.

In a preferred embodiment, a low molecular weight polymer (LVCR) is used as the polymer, and ICAM-1 is used as the drug. The LVCR is dissolved in water at a concentration of about 1% w/w, and ICAM-1 is added for a final 0.11% w/w ICAM-1 concentration. This leads to theoretical ICAM-1 loading in the final product of about 5%–15%, most preferably about 10%. Other percentages of both polymer and drug may be used, depending on the flow rates, the specific polymer, and the specific drug being loaded. The drug/polymer solution also may contain buffer salts of the type appropriate for the particular drug. For example, a TRIS or histidine buffer may be used in preparing and storing the ICAM-1, thus salts from those buffers will be present in the LVCR solution. These buffers also may be added to the drug/polymer solution to control the pH and possible degradation of the ICAM-1.

The preferred polymer used for forming the microparticles is sodium alginate, commercially available from Merck & Co., Inc. (Kelco Division, U.S.A., Rahway, N.J.), and most preferably a low molecular weight sodium alginate. Sodium alginates that may be used in practicing the present invention include: Keltone HV™, Keltone LV™, Kelgin HV™, Kelgin MV™, Kelgin LV™, Manucol DMF™, Manucol DH™, Manucol LD™, and Manugel DMB™, all of which are commercially available from Merck & Co., Kelco Division, U.S.A. Other alginates are available from Kibun Chemical Col or Pronova Biopolymers.

Other polymers may be used in practicing the present invention that have the desired release characteristics for the target drug being released from the microparticles, or that have desired bioadhesive properties as appropriate for a particular drug or delivery system.

Other polymers that may be used in the drug solution may include sodium calcium alginate, potassium alginate, propylene glycol alginates, xanthan gum, and gellan gum, hydrophilic cellulose polymers, and natural proteins, and synthetic polymers, among others. The selection of polymer will depend on the subject drug that is being loaded.

A drug used in a preferred embodiment of the system of the invention is t-ICAM-453, which was supplied by Bayer Corporation, Pittsburgh, Pa., as a 1–2% t-ICAM-453 solution buffered by TRIS-HCl. The drug may initially be presented frozen, freeze-dried or in a buffered solution at a concentration appropriate for the particular drug. The frozen drug samples then are added to the LVCR or other appropriate polymer solution.

In practicing the present invention, and referring to FIG. 1, the drug/polymer solution is pumped into the first mixing chamber (102) via a tube (not shown), preferably manufactured from a Teflon™ or other non-metallic material through the first port (104). The tube is secured within the port (104) at one end, and is connected to a flow-control pump (not shown) at the other end. The drug/polymer solution is introduced into the first mixing chamber (102) at a predetermined flow rate that produces a turbulence within the first chamber sufficient to create polymer droplets without significantly reducing the size of the particles.

An emulsifier substantially simultaneously is introduced into the first mixing chamber (102) via tubing (not shown) secured within the second port (106) at one end and controlled by a flow-control pump (not shown) at the other end. In a preferred embodiment for producing ICAM-1-loaded microparticles, the emulsifier is ethyl acetate, and most preferably a wetted ethyl acetate (about 2.8–3%). The emulsifier preferably is saturated (with water) to prevent the emulsifier from dehydrating the water-based solution of the drug and causing a build-up due to phase interactions between the emulsifier and the drug/polymer solution. Specifically, when using ethyl acetate in an ICAM-1 system, water from the drug/polymer solution is soluble in the ethyl acetate at concentrations less than 3%. In that instance, ethyl acetate is dehydrating the alginate emulsion and producing a highly viscous gel. That problem may be solved by pre-wetting the ethyl acetate to a level of about 2.8% or more before use. In other embodiments when the drug is not presented in a water-based solvent, it may be possible to use other, non-saturated, non-interacting emulsifiers.

In the ICAM-1 embodiment of the present invention, ethyl acetate is preferred as the emulsion-forming solvent because it is only partially miscible in water, is fully miscible with the cross-linking solvents, discussed in detail below, and is GRAS (i.e., Generally Recognized as Safe) status food grade, has a high purity, and is inexpensive.

In a system using 70/30 acetone/ethanol as the cross-linking solvent and using 0.5 mM TRIS solution concentration in LVCR/ICAM-1 buffered samples results in a 66% theoretical ICAM-1 loading. Using a 10 mM TRIS buffered sample results in 100% theoretical ICAM-1 loading. The effect of the buffer concentration on ICAM-1 loading in a pure ethanol system is not as dramatic. Under identical operating conditions, a 0.5 mM TRIS buffer produces 67% ICAM-1 loading and a 10 mM TRIS buffer produces 65% ICAM-1 loading.

In practicing the present invention, a buffer solution may initially be passed through the port (104) into the first mixing chamber (102) prior to introduction of either the drug/polymer solution or the emulsifier to pre-fill the mixing chamber and to prime the pumps associated with the system. When both the solution and the emulsifier are simultaneously introduced into the first mixing chamber (102) via the two ports (104, 106), an emulsion is formed. The turbulence created within the first mixing block (102) by the countervailing streams of solutions entering the first mixing block (102) breaks up the minor liquid (i.e., the LVCR) into individual droplets. The size of the droplets depends on the amount of turbulence in the chamber and properties of both liquids, which is related to the Reynolds number of the system at the chamber. The higher the Reynolds number, the smaller the microparticle size. In addition, the more viscous the two solutions, the more difficult it is to create turbulence.

Once the microparticles are formed in the first mixing chamber (102), they flow into a second mixing chamber (108). The second mixing chamber (108) preferably is adjacent to the first mixing block (102), to facilitate flow of the emulsion containing the microparticles. In a preferred embodiment, the second mixing chamber (108) is contiguous with the first mixing chamber (102), as illustrated in FIG. 1.

If the second mixing chamber (108) is not contiguous with the first mixing chamber (102), then the emulsion may be transferred from the first mixing chamber (102) into an enlarged second mixing chamber that contains an amount of a cross-linking agent. In such embodiment, the cross-linking occurs essentially simultaneously, i.e., less than about 2 seconds; however, residence time in the chamber may extend from a few hours to a few days, depending on the microparticle composition and the cross-linking agent to further dehydrate the microparticles.

If the second mixing chamber (108) is contiguous with the first mixing chamber (102), as illustrated in FIG. 1, the emulsion is transferred directly from the first mixing chamber (102) into the second mixing chamber (108). As the emulsion enters the chamber (108) via the third port (113), a stream of cross-linking agent solution is introduced at a predetermined flow rate into the second mixing chamber (108) via a fourth port (110). In a preferred embodiment, the fourth port (110) is perpendicular to the longitudinal axis of the mixing chamber (108) and off-set from the line of the emulsion stream, for introducing the cross-linking stream essentially tangential to the flow of the emulsion.

An important parameter in successfully manufacturing microparticles having the desired mean diameter and drug loading properties is the flow rate of the solutions introduced into the mixing chambers. In the system described in Example 1 for producing ICAM-1 loaded alginate microparticles, the drug/polymer solution flow rate into the first mixing chamber is between about 5 and 10 mL/min, and the emulsifier is introduced into the first mixing chamber at a flow rate of between about 50 and 80 mL/min. A series of runs using a 1% w/w LVCR solution, pre-wetted ethyl acetate, and a calcium chloride cross-linking agent were performed using the system of FIG. 1. After collection and drying, each sample was sieved through a 250 μm screen to segregate the larger particles from the bulk as an indicator of the amount of agglomeration occurring. The following Table 1 identifies the percent crushed product of less than 250 microns recovered.

TABLE 1

| Sample Number | LVCR Flowrate (mL/min) | EtOAc Flowrate (mL/min) | Cross-Linking Flowrate (mL/min) | % Crushed Product Sieved Less Than 250 μm |
|---|---|---|---|---|
| 1 | 10 | 50 | 70 | 95 |
| 2 | 10 | 30 | 70 | 0 |
| 3 | 10 | 80 | 70 | 84 |
| 4 | 15.3 | 50 | 70 | 92 |
| 5 | 15.3 | 30 | 70 | Flaky product |
| 6 | 15.3 | 80 | 70 | 41 |
| 7 | 24 | 60 | 70 | 90 |
| 8 | 24 | 80 | 70 | 71 |
| 9 | 37 | 50 | 70 | 74 |
| 10 | 37 | 80 | 70 | 31 |
| 11 | 25 | 60 | 40 | 66 |

Further analysis of particles having a size less than 250 microns were performed using both Malvern and Horiba size analysis: Malvern sizing is a known sizing technique based on laser diffraction principles using a Malvern 2600c droplet and particle sizer, available from Malvern Instruments Co., Inc. (Southborough, Mass.). Horiba analysis is a known sizing technique based on particle sedimentation techniques and is performed using a Horiba CAPA-700 particle size distribution analyzer, available from Horiba Instruments, Inc. (Irvine, Calif.). Particle sizing in the Horiba analyzer is based on aerodynamic properties of the particles, and results are reported as aerodynamic mass median diameter (AMMD) and percent of particles in representative size ranges. The following Table 2 presents the results of those analyses for selected samples from Table 1.

TABLE 2

| | Particle Sizing | | | | | |
| | Horiba | | | Malvern | | |
| Sample Number | Median (μm) | % <100 μm | % <10 μm | Median (μm) | % <100 μm | % <10 μm |
|---|---|---|---|---|---|---|
| 1 | 46.3 | 86.4 | 1.9 | 48.2 | 94.7 | 0.9 |
| 3 | 58.6 | 73.7 | 1.3 | 65.4 | 86.2 | 0.5 |
| 7 | 61.1 | 76.7 | 1.0 | 54.0 | 94.1 | 0.6 |

Preferably, the flow rate of the cross-linking agent is as low as possible to create enough turbulence within the second mixing chamber (108) to mix the microparticles with the cross-linking agent without generating excess turbulence to reduce the size of the particles. In a preferred embodiment, a 1% w/w LVCR with ICAM-1 is introduced into the first mixing chamber at a flow rate of about 5 mL/min. Pre-wetted (2.8% water) ethyl acetate is introduced into the first mixing chamber at a flow rate of about 83 mL/min.

The cross-linking agent may be any agent that reacts with the emulsifier to solidify the microparticles. In a preferred embodiment, calcium chloride is used as the cross-linking agent when aqueous sodium alginate is used to form the emulsion. Other calcium salts can be used, so long as they are soluble in the solvent or solvent mixture. In the cross-linking process, sodium in sodium alginate is replaced by calcium, making a non-water soluble calcium alginate microparticle loaded with ICAM-1. In that embodiment, the calcium salt is dissolved in an amount of a dehydrating solvent, such as acetone and ethyl alcohol which dehydrates the microparticles. Preferably the cross-linking solution includes an 0.8% $CaCl_2$ in 60% acetone and 40% ethanol.

In the ICAM-1/LVCR embodiment, calcium chloride is present in sufficient stoichiometric excess to completely cross-link the sodium alginate in the LVCR solution without producing a calcium chloride precipitate in the final product. In addition, if the calcium chloride concentrations are too high, an excessive amount of cross-linking results, preventing the formation of individual microparticles. The final product then is either a continuous matrix of cross-linked material or large (i.e., 1–2 mm) non-spherical particles.

Solvents that may be used with the cross-linking agent include acetone, which does not degrade ICAM-1 as readily as other solvents, such as isopropyl alcohol. Different solvents may be used in conjunction with other drugs, and may depend at least in part on the solubility of the subject drug. Each solvent has its advantages and disadvantages. Acetone readily dehydrates the cross-linked microparticles but does not dissolve calcium chloride. Ethanol is easily miscible with other solvents in the present system, and readily dissolves calcium chloride, but may result in lower drug loadings, for example when used in an ICAM-1 loading system, if the drug is soluble in ethanol. The use of isopropyl alcohol may result in a quick drying product that handles well, but may result in low drug loading. Using an acetone/ethanol combination, such as 85/15, 70/30, or 65/35, may lead to high loadings but have an increased production cost due to the use of two solvents.

Solvents are selected for their cost, suitability to the process, and existing common use in the pharmaceutical industry. Acetone may be mixed with ethanol rather than water, because water is mostly immiscible with the other process solvents and separates out in the final effluent. Such a phase separation is undesirable for ICAM-1 loaded microparticles because of the potential loss of ICAM-1 to the aqueous phase, agglomeration of the product, and incomplete dehydration. An amount of ethanol sufficient both to dissolve the calcium chloride and to prevent a two-phase mixture in the effluent is preferred.

An important factor in determining the success of the present system and method is the loading and yield of drug in the microparticles. For ICAM-1, the desired yield is greater than 80%. Losses in the overall yield include ICAM-1 lost in the process filtrate and the rinse filtrate, losses due to the de-activation of the ICAM-1, and losses in the microparticle fraction outside the desired microparticle size range.

ICAM-1 loading measurements may be determined by leaching the ICAM-1 from the microparticles or by dissolving the microparticles completely and analyzing the concentration by high pressure liquid chromatography (HPLC) or nephelometry, or by other methods that are or may become recognized in the relevant art.

Cross-linking solvents ethanol, 85/15 acetone/ethanol, 70/30 acetone/ethanol, 65/35 acetone/ethanol, and isopropanol may be used for an ICAM-1/sodium alginate system as described herein. The following Table 3 shows results obtained from runs using isopropanol, 70/30 acetone/ethanol, and ethanol as cross-linking agent solvents. Table 3 shows the fraction of particles less than 100 µm and the overall ICAM-1 yield, calculated by multiplying the fraction of ICAM-1 loading by the fraction of particles less than 100 µm.

As shown in Table 3, the 70/30 acetone/ethanol system yielded essentially a 100% loading of 10% ICAM-1, and 82% of the microparticles were less than 100 µm in diameter. The overall yield, as determined by the dry weight yield times sieving yield, was 82% of theoretical.

TABLE 3

ICAM-1 Loading for Isopropanol, 70/30 Acetone/Ethanol, and Ethanol, Cross-Linking Solution

| Sample Number | Cross-Link Solution | % ICAM-1 Loading | % Less Than 100 µm | % Overall ICAM-1 Yield |
|---|---|---|---|---|
| 1 | Isopropanol | 58 | — | — |
| 2 | 70/30 Acetone/ethanol | 100 | 82 | 82 |
| 3 | Ethanol | 65 | 98 | 84 |

In practicing the inventive system in a commercial environment, and as illustrated in FIG. 2, the drug/polymer solution, emulsifier, and cross-linking solutions each initially may be prepared in separate containers (202, 204, 206, respectively). Each of the solutions then may be transferred from the containers (202, 204, 206), using a control flow pump device (116), through an appropriate pore size sterile filter (208), e.g., 0.2 micron, and stored in separate sterile holding tanks (212, 214, 216, respectively). A second sterile filtration step may be included prior to introducing the solutions into the mixing block (100).

Using control flow pump devices (116), or a single control flow pump apparatus that has several inputs and outputs that allow separate flow rates for each solution, the solutions are pumped from the sterile holding tanks (212, 214, 216) and into the mixing block (100) via appropriate ports. Flexible tubing may be used to transfer the solutions from each container into the mixing block (100).

It may be preferable to prime the in-flow pump devices (116) with a buffer solution for each of the solutions being introduced into the mixing block (100). In-flow of the drug/polymer solution entering into the first mixing chamber (102) may begin prior to or after in-flow begins for the emulsifier. In certain circumstances it may increase the cost-effectiveness of the process to reduce the amount of wasted drug introduced into the mixing block (100) by initiating introducing the emulsifier into the first mixing chamber (102) prior to introducing the drug/polymer solution.

The flowchart of FIG. 3 outlines a preferred method of practicing the present invention. The drug/polymer solution is introduced (302) into the first mixing chamber (102) preferably simultaneously with the introduction (304) of the emulsifier into the first mixing chamber (102), thus forming (306) an emulsion containing the microparticles and solvent.

The emulsion then is transferred (308) into the second mixing chamber (108), at which time the cross-linking agent is introduced (310) into the chamber (108).

The length of time the emulsion remains in the first chamber and the cross-linked solution remains in the second chamber are a function of the flow-rates for the individual streams flowing into the respective chambers. Because both the formation of the microparticles and the cross-linking occur substantially instantaneously, i.e., in less than about 2 seconds, there is no requisite incubation period required in either chamber.

As the mixture of microparticles and cross-linking solvent exit the mixing block (100), the mixture is filtered (312) through a filter or sieve (218) that catches microparticles above a predetermined minimum range. In a preferred embodiment, microparticles containing ICAM-1 are filtered via a standard, commercial filter material. The filter may retrieve particles having a diameter of greater than about 20 µm, with microparticles of less than about 20 µm being washed out, possibly into a waste retrieval container (118). Alternatively, the filter (218) initially may filter out particles that are greater than, e.g., 200 µm, with a subsequent filtration to remove the smaller particles.

The particles in filter (218) then are subjected to a first wash (314). In one embodiment, and as shown in FIG. 2, the first wash step (314) involves using a control flow pump (116) to transport first wash solution from a container (224), through a sterile filter (208) and into a receptacle (226).

The first wash solution may be any dehydrating solution, such as an acetone, an alcohol, or a combination of both. A first wash of about 10% ethanol and about 90% acetone, or 90% isopropanol, or 90% ethyl acetate is preferred. Although some solutions may dehydrate the particular microparticle quickly and thoroughly, it is possible that some solutions may affect the efficacy of the drug loaded in the microparticles of interest. The first wash step (314) is intended to remove excess cross-linking agent, e.g., calcium chloride, without precipitation. The first wash step (314) also is intended to remove excess emulsifier, i.e., ethyl acetate.

Following the first wash step (314), preferably a second wash step (316) is performed in a similar fashion as the first wash step (314). That is, as shown in FIG. 2, a second wash solution is transferred via a flow-control pump device (116) from a container (228), through a sterile filter (208) and into a receptacle (230). The second wash step (316) may be performed using the same solutions as in the first wash step (314), or a variation. The solutions used in the second wash step (316) should also dehydrate the microparticles, thus such solutions may include neat acetone, isopropanol, or ethyl acetate, among others. The second wash step (316) is intended to remove the residue of the first wash solutions. Thus, a preferred second wash solution may be 100% acetone.

The microparticles may be recovered (232) using several methods known in the art. In a direct collection method, the sample is collected directly onto a Buchner funnel filter or other filter that can be used for commercial production. The filtrate is pulled through the filter via applied suction, and a cake of microparticles builds up as the product is collected on the filter.

Another collection method involves collecting the exit stream (i.e., microparticles and solvents) in a container, allowing the product to stand for a specified period of time (e.g., 0–48 hours), and then filtering the sample. The contact time of the microparticles to the solvent may potentially leach the drug or protein from the microparticles, but may provide additional dehydration of the microparticles when the solvent system used is one that has a high affinity for water.

The filter cake remaining on the filter after the second wash step (316) then may be collected and placed in a receptacle for a drying step (318). Preferably, the filtered substance is placed in a vacuum drying oven for an extended period of time, i.e., at about 50° C. for more than 8 hours. The amount of time, temperature, and vacuum depend on the specific composition of the microparticles and the production volume. However, the microparticles may rehydrate and regain as much as 5%–10% of their weight by exposure to humid room air.

As a final step, the dried particles may be deaggregated (320), for example, with a mortar and pestle system or any similar system adapted for commercial use, to a fine powder-like end-product and, if necessary, sieved to provide the desired size distribution. A desired end product of the process is an amount of non-agglomerated microparticles within the desired diameter range, and having a drug loading within the desired range.

The microparticle product may then be formulated, using standard formulations known and available to those skilled in the relevant art, for a nasal drug delivery device. The drug-loaded microparticles produced in accordance with the present invention have the properties of adhering to the nasal passageway, and gradually releasing the drug contained therewithin into the circulatory system of the recipient patient. The alginate in the microparticle interacts with the mucosa contained in the nasal passageway to become a gel-like substance which adheres to the surface of the nasal passageway as the drug is released.

In a preferred embodiment of a commercial scale manufacturing process using the present invention, the following quantities of components may be used for a 250 gram production run: about 35 grams of ICAM-1, about 70 liters of acetone, about 50 liters of ethanol, and about 120 liters of ethyl acetate for the process. The associated washing steps may require about 12 liters of acetone and about 1 liter of ethanol. Several mixing blocks of the type shown in FIG. 4 may be run in parallel to achieve a desired production run. Alternatively, various combinations of systems running in parallel also may operate for commercial production of ICAM-1-loaded calcium alginate microparticles.

The following non-limiting examples are representative embodiments of the inventive system and process described above.

EXAMPLES

Example 1

In this example, the effluent is 1% w/w LVCR and 0.11% ICAM-1, the emulsifier is pre-wetted (2.8% water) ethyl acetate, and the cross-linking solution 0.8% calcium chloride in ethanol. For LVCR loaded with ICAM-1, the desired particle diameter range is between about 20 μm and 80 μm, most preferably with a median between about 40 μm and 50 μm. The desired ICAM-1 loading is about 10%, and the target recovery is about 80% to about 100%.

Using the mixing block shown in FIG. 4, the LVCR stream flow rate is varied from 15 to 45 milliliters per minute (mL/min) and the ethyl acetate stream flow rate is varied form 61 to 106 mL/min. Table 4 presents representative sample data obtained using these parameters.

TABLE 4

| Sample Number | Flows mL/min | | Cross-Linking | Malvern Particle Sizing | | |
| --- | --- | --- | --- | --- | --- | --- |
| | LVCR | EtOAc | | Median (μm) | % Less Than 104 μm | % Less Than 8.8 μm |
| 1 | 15 | 61 | 70 | 88.4 | 63.8 | 0.3 |
| 2 | 22 | 68 | 70 | 95.0 | 58.8 | 0.3 |
| 3 | 28 | 73 | 70 | 100.6 | 53.4 | 0.2 |

Example 2

A series of tests were run to determine whether the diameter of the port used for introducing the effluent stream into the first mixing chamber had any effect on the size and distribution of the produced microparticles.

The tests were run using the system illustrated in FIG. 4, and a 1% w/w LVCR solution. The inner diameter of the LVCR port was increased from 0.034 cm to 0.069 cm, and the flow rates of the LVCR solution and the ethyl acetate solutions were varied. The flow rate of the cross-linking agent was maintained as a constant. The results of such tests are shown in the following Table 5:

TABLE 5

Operating Conditions and Sieving Results

| Sample Number | LVCR Hole Diameter (Inches) | Flows mL/min | | Cross-Linking | % Less Than 100 μm | % Less Than 250 μm |
| --- | --- | --- | --- | --- | --- | --- |
| | | LVCR | EtOAc | | | |
| 1 | 0.0135 | 28 | 89 | 70 | 27.9 | 40.2 |
| 2 | 0.0135 | 28 | 72 | 70 | 49.5 | 74.6 |
| 3 | 0.0135 | 31 | 72 | 70 | 17.9 | 64.0 |
| 4 | 0.0135 | 29 | 72 | 70 | 31.3 | 74.4 |
| 5 | 0.027 | 28 | 72 | 70 | 16.9 | 40.2 |
| 6 | 0.027 | 31 | 72 | 70 | 34.8 | 50.4 |
| 7 | 0.027 | 31 | 56 | 70 | 17.8 | 46.5 |
| 8 | 0.0135 | 14 | 62 | 70 | 49.5 | 95.7 |
| 9 | 0.0135 | 28 | 72 | 70 | 46.7 | 85.3 |

The results in Table 5 show that in all instances, over 15% of the particles were greater than 100 μm, and in some cases nearly 50% of the particles were over 100 μm in diameter. The results indicate that the particle size is not solely dependent on the LVCR port diameter. Other parameters, such as inner diameter of the mixing chamber, flow rate, and internal turbulence, may be additional factors affecting particle size.

Example 3

Isopropyl alcohol was used as the cross-linking solvent for an ICAM-1/LVCR solution. Data indicate that microparticles produced using isopropyl alcohol as the cross-linking solvent dry more quickly and handle better than microparticles produced using acetone or other alcohols.

In this example, a LVCR flow rate of 14 mL/min and an ethyl acetate flow rate of 65 mL/min were used in the block of FIG. 4. Using unloaded polymer solutions, it was possible to produce 45 grams of unloaded microparticles in under 5 hours (i.e., a rate of 0.16 g/min). Of the 45 grams collected, 37.2 grams, i.e., 83%, were smaller than 100 μm.

Particle sizing on a Horiba apparatus of the particles sieved through a 100 μm screen produced a median size of 47 μm, with 89% being less than 100 μm and 4.4% being less than 10 μm. Thus, particles having the desired median diameter size range of 40 μm to 50 μm was achieved for non-loaded LVCR.

Example 4

A set of 50 gram bulk runs were made using LVCR both with and without ICAM-1 to test the longevity of the inventive system during a run. In this example, wet (2.8% water) ethyl acetate was used as the emulsifier and 1% w/w LVCR were used. The set flow rate for the LVCR stream was 15.5 mL/min, and the set flow rate for the ethyl acetate and cross-linking solution streams was 70 mL/min. The LVCR solution was buffered with either 10 mM histidine or 10 mM TRIS and, when ICAM-1 was used, the LVCR solution also contained 2.3% (w/v) of 10% ICAM-1 by weight.

The results of these runs are summarized in Table 6 below.

TABLE 6

| Sample Number | Buffer | Cross-Linking Solution | % Theoretical ICAM-1 Loading | wt % Product <100 μm |
|---|---|---|---|---|
| 1 | TRIS, 10 mM | 70/30 Acetone/EtOH | 91 | 92 |
| 2 | Histidine, 10 mM | 70/30 Acetone/EtOH | 81 | 94 |
| 3 | Histidine, 10 mM | 65/35 Acetone/EtOH | 78 | 98 |
| 4 | Histidine, 10 mM | 65/35 Acetone/EtOH | 67 | 86 |
| 5 | Histidine, 10 mM | 60/40 Acetone/EtOH | 86 | 77 |
| 6 | Histidine, 10 mM | 60/40 Acetone/EtOH | 93 | 50 |
| 7 | Histidine, 10 mM | 60/40 Acetone/EtOH | No ICAM | 92 |
| 8 | Histidine, 10 mM | 60/40 Acetone/EtOH | No ICAM | 76 |

As shown in that Table 6, the ICAM-1 loading in the histidine samples is in as that of the TRIS sample. The other entries show that as the ratio of acetone to ethanol changes, the loading still remained about 80% theoretical. The ICAM-1 loading of the samples was reproducibly above 75% of theoretical loading.

Example 5

In this example, samples that had initially been dried for 12 hours or 3 days in a vacuum oven were redried in the oven for an additional 4 hours or 10 hours, respectively. After redrying, they were weighed, allowed to equilibrate to room conditions and weighed again. The following Table 7 shows the results of these drying studies.

TABLE 7

Loss on Second Drying

| Sample Number | Initial Drying Time | rH % During Initial Weighing | Second Drying Time | rH % During Second Weighing | % Mass Lost on Second Drying | % Mass Loss After Allowing to Come to Equilibrium |
|---|---|---|---|---|---|---|
| 1 | 12 h | 48 | 4 h | N/A | 13.2 | — |
| 2 | 12 h | 48 | 4 h | N/A | 12.9 | — |
| 3 | 12 h | 48 | 4 h | N/A | 8.8 | — |
| 4 | 3 days | 30 | 10 h | 33 | 3.1 | −2.5 |
| 5 | 3 days | 30 | 10 h | 33 | −0.1 | −7.4 |
| 6 | 3 days | 30 | 10 h | 33 | 28.7 | 20.5 |

Samples that initially were dried for 12 hours lost about 10% water upon re-drying. However, these samples initially had been processed under humid conditions (i.e., 48% rH) and could have lost only the water gained during processing. Samples dried initially for 3 days showed variable results. In some instances, essentially no water loss was detected following a second drying. However, in other instances, substantial weight loss was observed following a second drying. In all samples, the microparticles gained weight after reaching equilibrium at room conditions.

While the present invention has been described in terms of specific methods and compositions, it is understood that variations and modifications will occur to those skilled in the art upon consideration of the present invention.

For example, it is anticipated that smaller protein fragments and peptides derived from ICAM-1 that still contain the virus-binding site would be effective for encapsulation and delivery as described herein.

Although the preferred form of the present invention is described in terms of t-ICAM-453 in an alginate microparticle, it is anticipated that other proteins and polypeptides may be suitable for loading in an alginate microparticle, and that ICAM-1 may be used in conjunction with a material other than alginate. It is anticipated that the general method and system of the invention for producing ICAM-1 loaded microparticles can be used to prepare other microparticles loaded with numerous other drugs.

Numerous modifications and variations in the invention as described in the above illustrative examples are expected to occur to those skilled in the art and consequently only such limitations as appear in the appended claims should be placed thereon.

Accordingly, it is intended in the appended claims to cover all such equivalent variations which come within the scope of the invention as claimed.

What is claimed is:

1. An ICAM-1 formulation for nasal delivery, said formulation comprising a compatible diluent and microparticles comprising starch and ICAM-1, said particles having a controlled size range, such that a high percentage of the microparticles have aerodynamic mass median diameter between about 20 μm and 80 μm, whereby microparticles are deposited in the nasal cavity and yield a sustained, controlled release of ICAM-1 over several hours.

2. The ICAM-1 formulation of claim 1, wherein said ICAM-1 consists of one of more biologically active fragments of ICAM-1, one or more functional domains of ICAM-1, analogs of said biologically active ICAM-1 fragments, or combinations or derivatives thereof.

3. A drug formulation for nasal delivery, said formulation comprising a compatible diluent and microparticles comprising starch and a drug, said particles having a controlled size range, such that a high percentage of microparticles have an aerodynamic mass median diameter between about 20 μm and 80 μm.

* * * * *